United States Patent [19]
Chapman et al.

[11] Patent Number: 6,023,456
[45] Date of Patent: Feb. 8, 2000

[54] DYNAMIC TRAFFIC CONDITIONING

[75] Inventors: Alan Stanley John Chapman, Kanata, Canada; Hsiang-Tsung Kung, Lexington, Mass.

[73] Assignee: Nortel Networks Corporation, Montreal, Canada

[21] Appl. No.: 08/818,612

[22] Filed: Mar. 14, 1997

Related U.S. Application Data

[63] Continuation-in-part of application No. 08/772,256, Dec. 23, 1996.

[51] Int. Cl.$^7$ ........................................ H04J 3/26
[52] U.S. Cl. ........................... 370/252; 370/401; 370/469
[58] Field of Search ................... 370/230, 235, 370/252, 253, 389, 400, 401, 412, 465, 468, 469; 395/200.53, 200.54, 200.56, 200.55, 200.7

[56] References Cited

U.S. PATENT DOCUMENTS

| | | | |
|---|---|---|---|
| 4,914,650 | 4/1990 | Sriram | 370/412 |
| 5,268,900 | 12/1993 | Hluchy et al. | 370/412 |
| 5,408,465 | 4/1995 | Gusella et al. | 370/252 |
| 5,487,061 | 1/1996 | Bray | 370/252 |
| 5,526,350 | 6/1996 | Gittins et al. | 370/468 |
| 5,673,253 | 9/1997 | Shaffer | 370/468 |
| 5,699,361 | 12/1997 | Ding et al. | 370/431 |

FOREIGN PATENT DOCUMENTS 0 706 297   4/1996   European Pat. Off. .

OTHER PUBLICATIONS

P. Newman et al., Flow Labelled IP: A Connectionless Approach to ATM, pp. 1251–1260, Mar. 1996.

S. Damaskos et al., The Berkom–II FlowSpec and its Mapping on ATM, pp. 141–146, May 1994.

*Primary Examiner*—Ricky Ngo
*Attorney, Agent, or Firm*—Foley & Lardner

[57] ABSTRACT

Multi-media networks will require that a data flow be given certain quality-of-service (QOS) for a network connection but pre-negotiation of this sort is foreign to the current data networking model. The real time traffic flow in the data network requires distinct limits on the tolerance to delay, and the variations in that delay. Interactive voice and video demand that the total delay does not exceed the threshold beyond which human interaction is unacceptably impaired. The present invention allows the network to discover the nature of the service for each traffic flow, classifies it dynamically, and exercises traffic conditioning by means of such techniques as admission control and scheduling when delivering the traffic downstream to support the service appropriately.

13 Claims, 6 Drawing Sheets

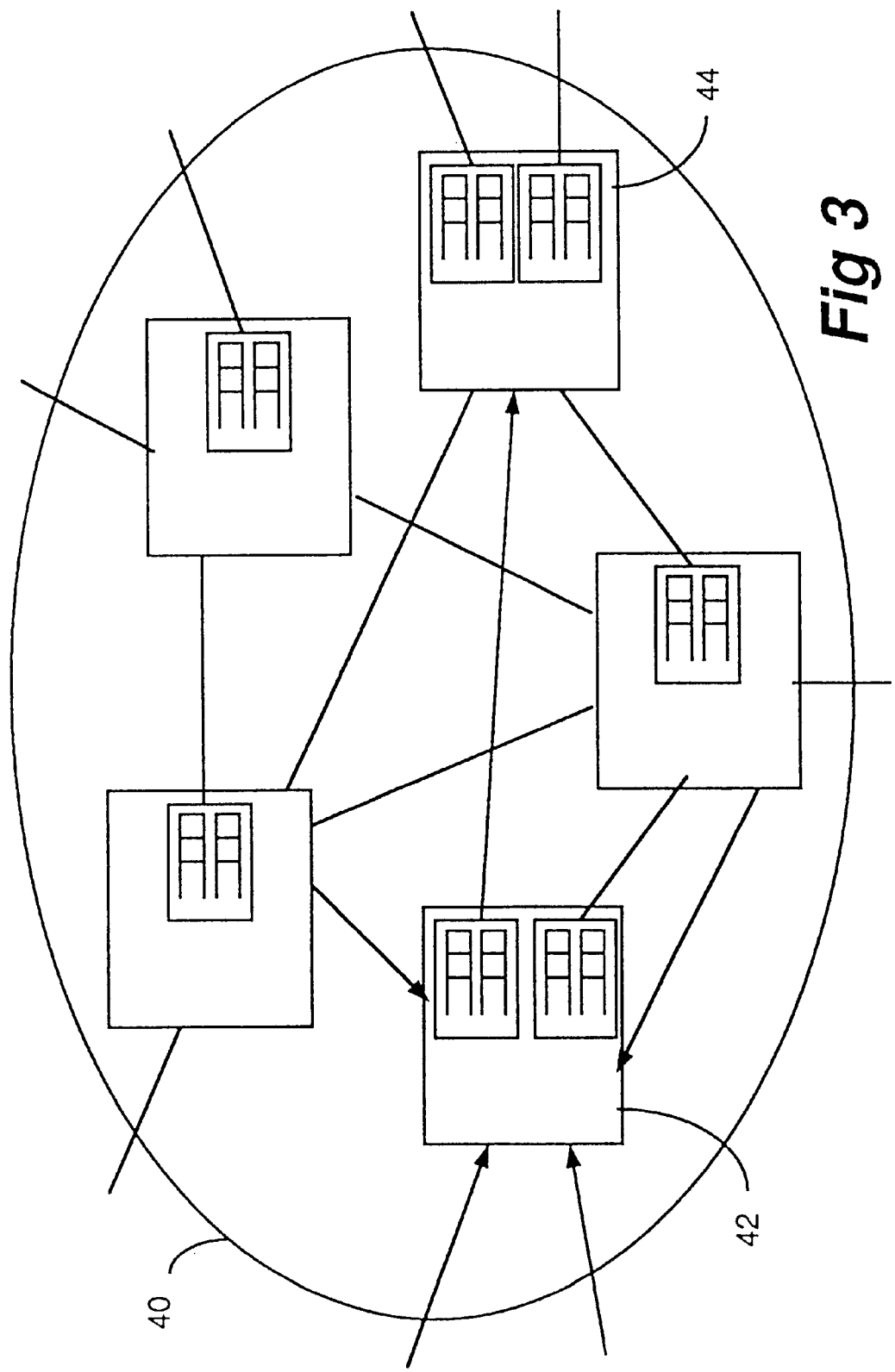

DYNAMIC TRAFFIC CONDITIONING

This is a continuation-in-part of Application Ser. No. 08/772,256, filed on Dec. 23, 1996.

FIELD OF THE INVENTION

The invention relates generally to the conditioning of traffic at a node of a data network. In particular, it is directed to a technique by which the traffic is dynamically classified at a node and delivered downstream according to the Quality of Service (QOS) specified by the assigned class or by such a network administrator as the network operator.

BACKGROUND OF THE INVENTION

Multi-media networks will require that a data flow be given certain QOS for a network connection. The recently proposed resource reservation protocol (RSVP) for IP (and signalling in ATM networks) is a way of requesting a particular QOS but pre-negotiation of this sort is foreign to the current data networking model and would require changes at the application level.

The major driving force behind the requirement for different QOSs in the data network is the need to introduce real time flows which have distinct limits in the tolerance to delay, and the variations in that delay. Interactive voice and video demand that the total delay does not exceed the threshold beyond which the human interaction is unacceptably impaired. Non-interactive voice and video streams which are being transferred in real time require that the maximum delay variation is bounded so that buffers can be kept to a reasonable size and guaranteed not to underflow. Meeting the delay requirements for real time flows usually means that these flows must be given priority over other traffic. This in turn brings in a requirement to limit the amount of such high priority traffic by some admission control policy to ensure that other classes of traffic do get some of the available bandwidth.

There are applications other than voice and video that can benefit from controlled latency. Network control traffic such as DNS transactions represent a small fraction of the total but will provide a much improved performance if treated with priority.

There is another class of traffic which does not have the tight requirements of voice or video but does involve human interaction with computers and can lead to noticeable decreases in productivity (or increases in frustration) if subjected to long delays. This traffic type is generated by applications such as X-Windows, Telnet and, more often now, world wide web browsing. This traffic can be protected from long queuing delays caused by bulk transfers such as FTP or NFS by allocating to it some guaranteed portion of the bandwidth as part of an output scheduling policy.

Even the bulk traffic can suffer from too much competition. Often a file transfer will be aborted after using much network resource because the overall time has exceeded the delay tolerance of the application or the user or management policies in intermediate servers. Also, when congestion causes packets to be dropped, it can easily impact many flows, and cause many resends. By guaranteeing a certain number of flows a minimum bandwidth and treating the remainder as best effort, it is possible to avoid spreading packet loss over so many flows and to reduce the number of aborted flows.

It would be much more acceptable if the QOS requirements were met by the network automatically and dynamically without the need for signalling. This would fit more naturally with the current IP networking paradigm.

Traditionally, Internet services (such as FTP, Telnet, NFS) are known only to the end systems and not to the network itself. The present invention allows the network to discover the nature of the service for each traffic flow, classify it dynamically and exercise traffic conditioning by means of such techniques as admission control and scheduling when delivering the traffic downstream to support the service appropriately. The scheduling separates real time traffic from other traffic by priority and allocates bandwidth between various classes of traffic. In conjunction with scheduling, the admission control guarantees performance. The scheduling also allows implementation of overlay administrative policies to give, for instance, certain groups different treatment than other groups. The classification need not emulate precisely the effect of pre-negotiated network connections but should provide similar improvements in service quality as seen by the users and the network.

It should of course be noted that in this specification the data network can also include any packet-based or cell-based networks, including ATM networks.

OBJECTS OF INVENTION

It is therefore an object of the invention to provide a method of and an apparatus for dynamically conditioning traffic at a node of a data network.

It is a further object of the invention to provide a method of and apparatus for continuously monitoring and dynamically classifying traffic into one of a plurality of preset classes according to a set of classification parameters.

It is another object of the invention to provide a method of and apparatus for controlling the delivery of the traffic downstream according to quality of service parameters specified by the dynamically selected class.

SUMMARY OF THE INVENTION

Briefly stated, the invention resides in a packet data network for multimedia traffic having one or more nodes. According to one aspect, a method of dynamically conditioning traffic comprises steps of continuously monitoring the traffic at a node as to its traffic characteristics and classifying the traffic into one of a plurality of classes according to preset criteria of traffic characteristics. The method further includes a step of delivering the traffic downstream according to the quality of service specified by one of the plurality of classes.

According to another aspect, the invention is directed to a method of dynamically conditioning traffic comprising steps of continuously monitoring the traffic at a node to detect a real time traffic flow and determining if the real time traffic flow can be admitted for delivery downstream, based on the available bandwidth of the data network. The method includes another step of reclassifying the real time traffic into a different class for delivery downstream according to a quality of service specified by the different class.

BRIEF DESCRIPTION OF DRAWINGS

FIGS. 2 and 3 show possible locations of traffic conditioners of the invention.

DETAILED DESCRIPTION OF THE PREFERRED EMBODIMENTS OF THE INVENTION

Figure 1:
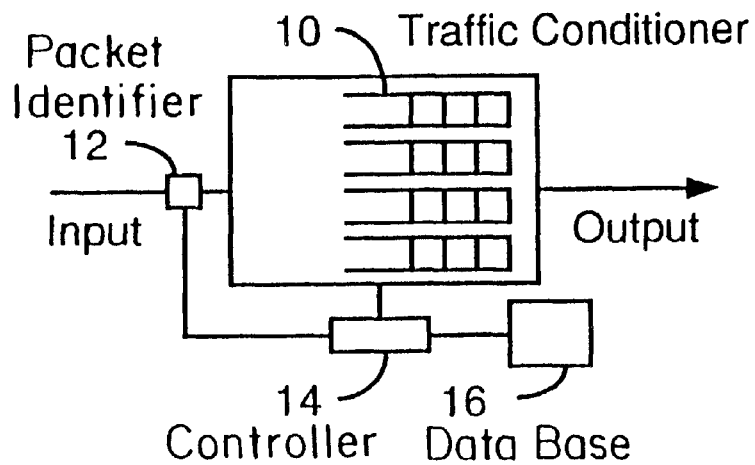
FIG. 1 is a schematic diagram of the traffic conditioner according to an embodiment of the invention.

Referring to FIG. 1, the traffic conditioner, according to one embodiment of the invention, includes a plurality of queues 10, at least one for each class. It is located at a node of a data network. Every packet of an input stream is inspected and identified at 12 using, for example, IP addresses, ports and protocol. A controller 14 characterises the flow (using rate, duration, etc.) and assigns it a class. A plurality of classes are envisioned according to embodiments of the invention and will be described later. The controller refers to a database 16 and uses output scheduling to allocate bandwidth among classes and implements an admission control policy for a class before delivering an output stream toward downstream nodes or to peripherals. It also discards packets from non-admitted flows and passes on flow classification to downstream nodes.

Figure 2:
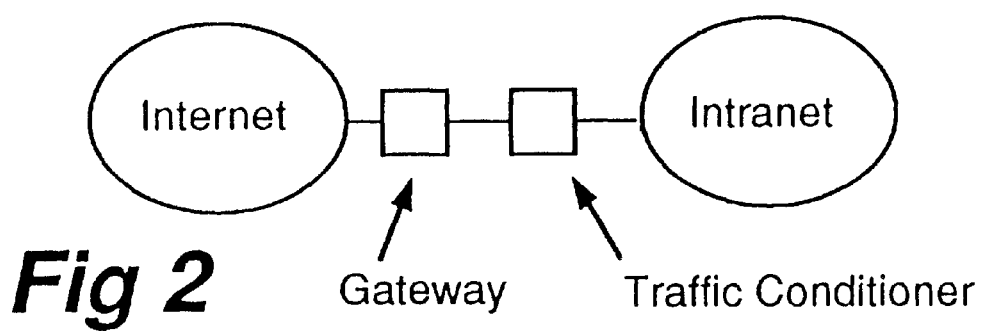
Figure 4:
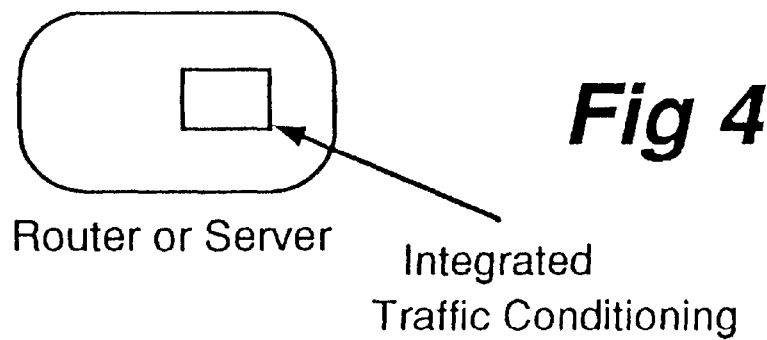
FIG. 4 illustrates that the traffic conditioning features of the invention can be installed at a router or a switch.

The traffic conditioning of the invention can take place at various places in the data network. For example, as gateways are often a bottleneck and bulk flows can decrease response times for interactive users, a traffic conditioner can be located at a place shown in FIG. 2 which will alleviate this problem. In FIG. 3, traffic conditioners are located at a plurality of IP switches which form a data network 40. Packet switches will not be able to provide good performance for new services, such as real time video, unless traffic conditioning is implemented. A conditioner at an output port of a switch 42 monitors and controls all the traffic which comes into the switch and goes out of this output port to the downstream node 44. An integrated traffic conditioning feature can be installed at a router or a server as shown in FIG. 4.

In one instance of IP networking, the identifying individual traffic flow is simple. It only requires inspection of addresses and protocol port number for both source and destination. This approach has been used for some time in other applications such as TCP Routing and, more recently, in IP switching.

Any scheme which characterises and classifies flows for differing treatment should be capable of modification to suit the particular operating environment. According to one embodiment, the following six classes of traffic flow which could be used in a typical TCP/IP based network are considered and described in detail below.

(Class 1)—Interactive Users (TCP)

This class is intended to capture TCP flows for such applications as X-windows, Telnet and lightweight web browsing. Telnet and X-windows can be very long sessions but have predominantly short packets. In this embodiment, this classification defines a short packet as less than or equal to 128 Bytes and a long packet as greater than 128 Bytes. Web browsing has a mixture of packet sizes and transaction lengths and can cause flows of long packets, particularly while loading image files. This class is the default one for TCP flows but when the flow contains a long series (e.g., 200) of long packets without an intervening series of two or more short packets, it is considered to be bulk transfer and no longer valid for this class. A TCP bulk flow may occasionally include short packets, containing only the TCP ACK message or the tail end of a sending buffer. Thus, unless the short packets are in a series of two or more in number, the flow is still considered to be bulk transfer.

(Class 2)—Bulk Transfer with Guaranteed Bandwidth (TCP)

If TCP traffic is not interactive, it is classified as bulk transfer. Some of the bulk transfer flows are admitted to a scheduling class which has a protected portion of the bandwidth and a limited number of members such that some minimum bandwidth is guaranteed for these flows.

(Class 3)—Bulk Transfer, Best Effort (TCP)

Any bulk TCP flows which are not admissible to the guaranteed bandwidth class are treated in this class on a best effort basis. Classes (2) and (3) are intended to handle large FTP or large web images.

(Class 4)—Low Latency (UDP)

This class contains flows which require very low bandwidth. In general, these flows consist of low bandwidth voice, NFS requests, short NFS replies, and network control packets such as DNS transactions. Most real time voice will be continuous flow UDP (User Datagram Protocol) at less than 20 packets per second. This is the default class for UDP and flows above a threshold bandwidth are moved out fast. There would be an admission control policy such that if the allocated bandwidth for this class is used up, new flows would be moved to the best effort class.

(Class 5)—Real Time (UDP)

Any flow with real time characteristics which will be defined below and a bandwidth too high for the low latency class will be captured in this class. High bandwidth voice and streaming video are the expected members. For example, video will be a continuous UDP flow at up to 4Mb/s=(1000 pps). Flows exhibiting real time characteristics but for which there is no resource under the admission control policy, would be rejected and subsequent packets discarded.

(Class 6)—Bulk Best Effort (UDP)

All other UDP flows will be grouped into this class. Expected members are NFS file copy and backup sessions characterised by many long packets at a substantial rate.

In summary, according to this embodiment, discrimination between traffic types is based on simple analysis of packet arrival rates and packet length plus a particular test for real time UDP traffic which will be described below. The characteristics of a flow are monitored continuously and the flow can be re-classified during its lifetime. The ability to re-classify also covers the cases where consecutive flows assume the same identity but have different characteristics.

It is possible to use port number information in some instances to determine service type and complement the dynamic classification described above. For example, TCP port 23 is the well known port for the telnet server. Since a telnet session always carries interactive traffic, it is possible to classify any TCP flow with one of its port number being 23 as TCP interactive. However, a single port number can sometimes be used for multiple services of varying nature. For instance, the TCP port number 80, reserved for the HTTP server, could be used for both TCP Interactive and TCP Bulk. A classification scheme should use static information in the packet header such as port number and protocol types, as well as the information collected dynamically.

Figure 5:
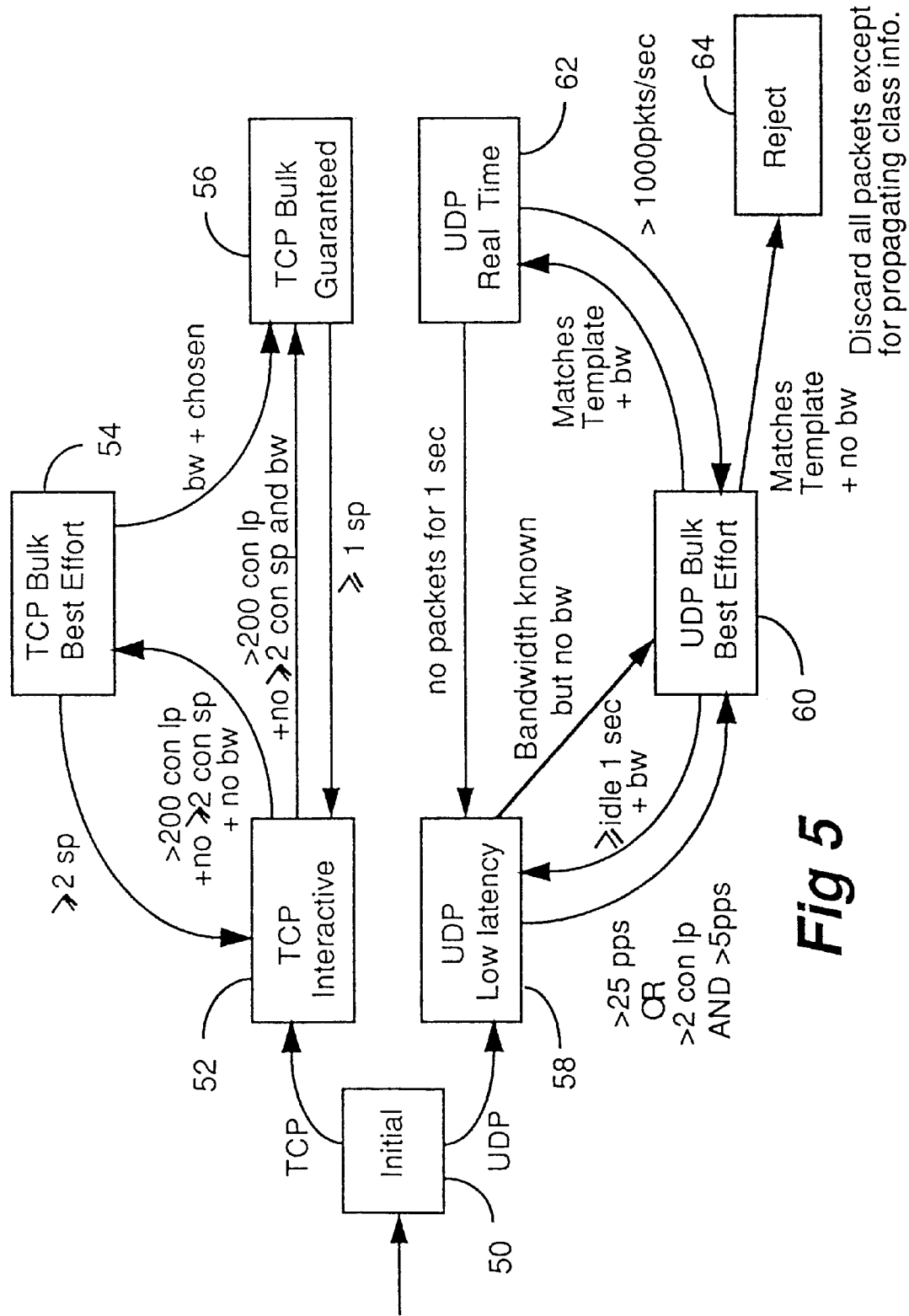
FIG. 5 is a pictorial view of state transitions.

FIG. 5 is a pictorial view of state transitions involving these classes according to the embodiment. In the figure, the following abbreviations are used:

```
p        = packet
sp       = short packet
lp       = long packet
con lp   = consecutive long packets
bw       = bandwidth available
chosen   = chosen by policy
pps      = packets per second arrival
```

The following criteria are also applied:

(a) For all classes, return to initial if there are no packets for 30 seconds.

(b) For all flows, check option field and if class is defined then force the flow to that class for 100 packets or 30 seconds.

Referring to FIG. 5, the state machine contains the following states:

(A) Initial
(B) TCP Interactive
(C) TCP Bulk Best Effort
(D) TCP Bulk Guaranteed
(E) UDP Low Latency
(F) UDP Real Time
(G) UDP Bulk Best Effort
(H) Reject In the following detailed description, ">" indicates "true" for all the states.

Power Up >[Idle for 30 seconds]--> Initial If class information is received from upstream then force that state for 100 packets. After 100 packets or 30 seconds with no information, revert to local judgement.

```
> Initial (at 50 in Figure 5)
    > [Protocol=TCP] --> TCP Interactive
    > [Protocol=UDP] --> UDP Low Latency
> TCP Interactive (at 52)
    > [200 consecutive long packets each of size > 128 bytes without
      an intervening series of two or more short packets]
        > [Some TCP Bulk min bandwidth available]
            --> TCP Bulk Guaranteed
        > [Otherwise]
            --> TCP Bulk Best Effort
> TCP Bulk Best Effort (at 54)
    > [Departure of a flow from TCP Bulk Guaranteed] and [Picked by
      a Policy]
        --> TCP Bulk Guaranteed
    > [Two consecutive short packets of size no greater than 128
      bytes]
        --> TCP Interactive
> TCP Bulk Guaranteed (at 56)
    > [Two consecutive short packets of size less than 128 bytes]
        --> TCP Interactive
> UDP Low Latency (at 58)
    > [After any 1 second in the state, and > 25 packets have arrived]
        --> UDP Bulk Best Effort
    or
    > [Two or more consecutive long packets] and [>5 packets in 1
      second]
        --> UDP Bulk Best Effort
    > [Bandwidth is known] and [no more bandwidth available]
        --> UDP Bulk Best Effort
> UDP Bulk Best Effort (at 60)
    > [Matches real time template] and [bandwidth available in UDP
      video]
```

```
        --> UDP Real Time
        > [Otherwise]            --> Reject
    > [Idle for more than one second] and [bandwidth available]
        -> UDP Low Latency
> UDP Real Time (at 62)
    > [300th packet arrives in time < 200 ms]
        --> UDP Bulk Best Effort
    > [Idle for 1 second]
        --> UDP Low Latency
> Reject (at 64)
    Discard all packets except those used for propagating REJECT
    information.
```

Real Time Flow Detection

As described earlier, it is necessary to distinguish real-time traffic from other BULK UDP flows. It is reasonable to assume at the present state of the art that NFS represents the only UDP traffic which is bulk and not real-time. Then an easy way is to inspect the port numbers of the flow in question. If neither of them is 2049, the reserved port number for NFS servers, then the flow is classified as Real Time.

Similarly, if it can be assumed that real-time flows of interest all use servers with reserved port numbers, then they can be classified by the static information on port numbers. Today, most of real-time audio and video servers appear to use a set of special ports which can be easily recognized.

For circumstances where these assumptions don't apply, it is necessary to provide a dynamic method to identify real time flows. The major difference between real time UDP flows and other UDP applications such as NFS is that (a) real time streams are not self-clocked, that is, the packets are sent continuously without acknowledgements from the receiver, and (b) the average packet generation rate is a constant.

There are two ways in which these attributes can be used to detect the real time flow. Under congestion conditions, the queue for a real time flow will grow without bound whereas the queue for a self-clocked flow will only grow to the size of an acknowledged burst (the maximum burst without acknowledgement is 8 Kbytes for NFS). Another approach is to keep a history of interarrival times for the packets of a flow. Self-clocked flows will exhibit a bi-modal distribution whereas the real time streams will be uni-modal around the average rate. In one embodiment, this approach can be implemented by using a threshold that is set to a value somewhat more than the average interarrival time. Two counts are kept; one of interarrival times below the threshold and one for interarrival times above the threshold. If the second count is more than a certain value e.g., 10% of the first count then the flow is classed as non-real time. This second method may be preferred since it does not require waiting for congestion to identify the stream. Quick admission or rejection of the flow is important.

Scheduling Flows

There are various techniques available for scheduling multiple queues at output ports of a switching node. In any case, typically, the real time and low latency classes described above would be given absolute priority (hence the need for admission control), and the other classes would be scheduled in a way which allocates to them the proportion of the bandwidth allocated by the network administrator.

Figure 6:
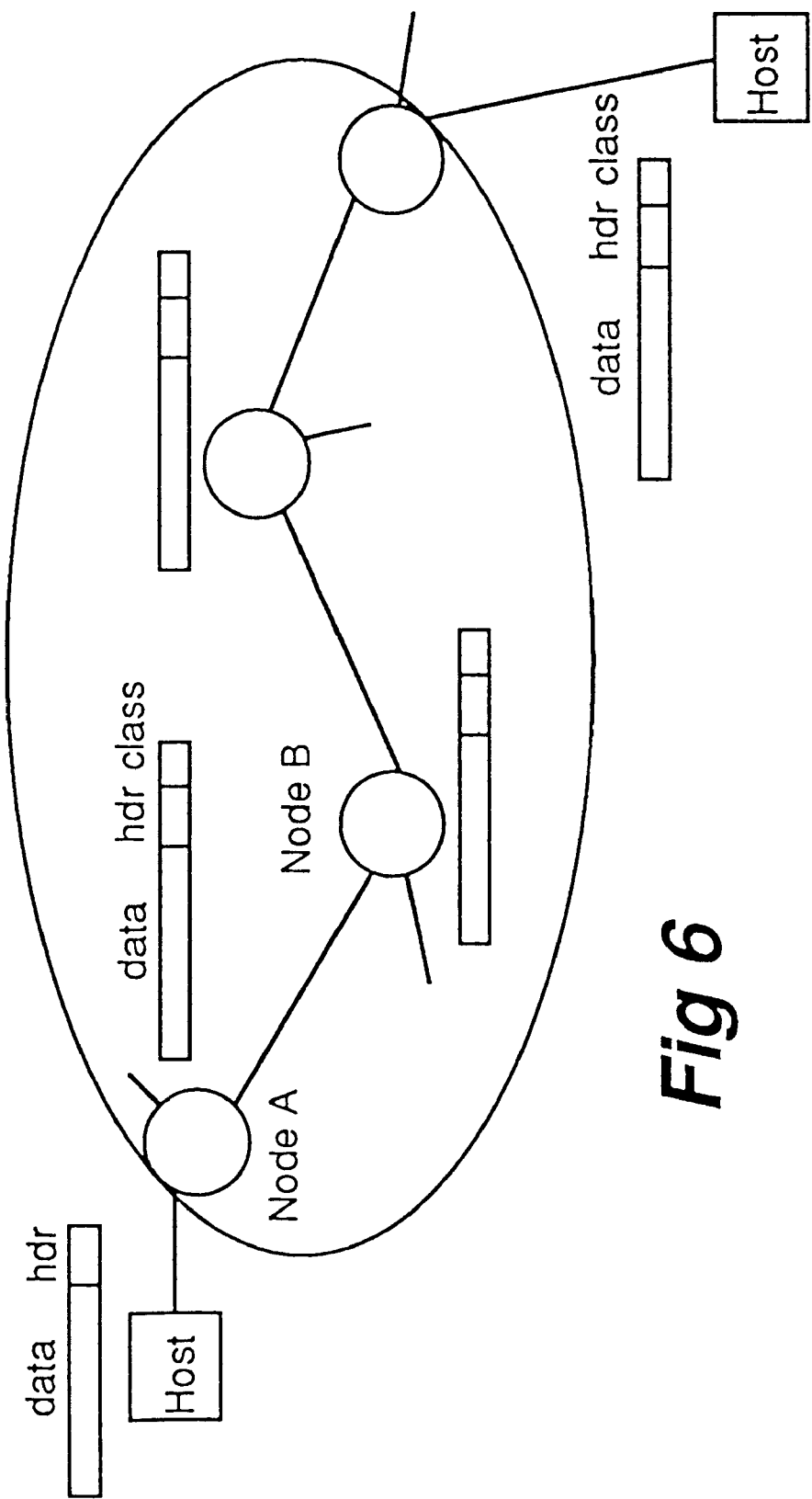
FIG. 6 shows classification information being propagated downstream.

Referring to FIG. 6, in a further embodiment, instead of each node performing the above classification autonomously as described thus far, the first node (node A) on the route passes on its findings to the downstream nodes and provides more efficient traffic conditioning. In yet a further embodiment, there is no reason that the source host machine cannot be considered the first node which classifies the traffic and sends the classification to nodes along the route. These downstream nodes can then use the acquired knowledge instead of local classification and give the flow a consistent treatment throughout its path. They accept the upstream classification until it expires and propagate it downstream. The information can be propagated in various ways, but in one way it could be carried in the flow by inserting information in one or more packets in the flow (for example, by an entry in the IP option field). Every n-th packet could carry the information and the downstream node would act on that information until it aged out after a multiple of n packets. In an ATM based network, the classification could be implied by the VPI/VCI value chosen for the flow.

Figure 7:
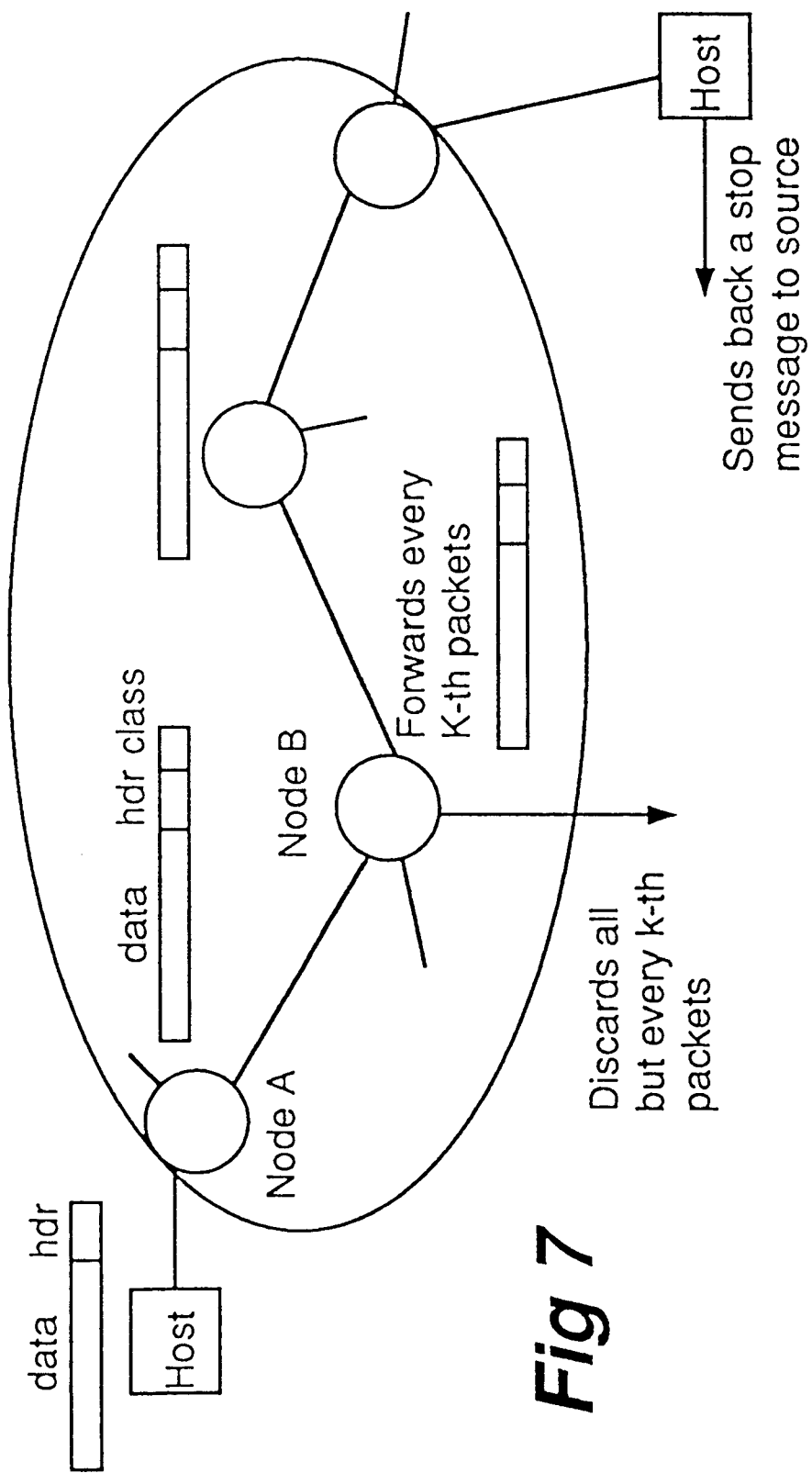
FIG. 7 shows that the REJECT information is being passed forward and reflected back to the source host.
Figure 8:
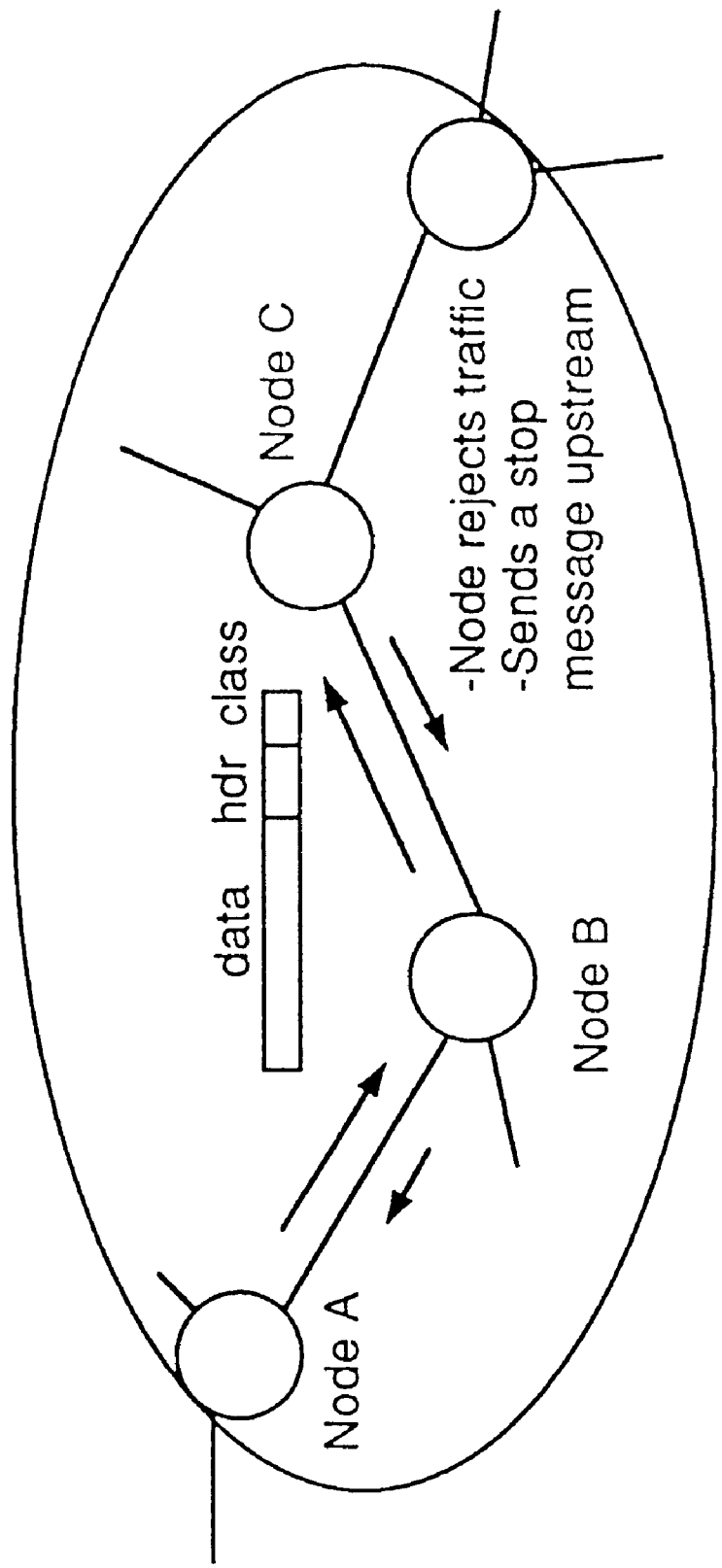
FIG. 8 shows a circumstance in which a stop message is sent back upstream from a node.

Referring to FIG. 7, the classification REJECT can be reflected back from the destination host to the source host, thus improving the efficiency of the network. To facilitate this, not all packets from the flow would be discarded. Instead, every k-th packet would be passed onward with the classification in the option field. For example, node B determines that the packet must be rejected for whatever the reason, it discards all but every k-th packet, which is forwarded to the destination host, which in turn sends a message to the source host to stop. In another scenario as shown in FIG. 8, instead of the host, a node which rejects the traffic stream for some reason can send a message back upstream indicating that the traffic has been rejected and should therefore be stopped.

Complexity

In any network where different qualities of service are being supported, there has to be some process to classify the flow attributes and then a way of verifying that the flow is adhering to the attributes. This verification, or policing, can be done at the edges of a subnet or at every node. The method described here uses the mechanisms that would be in place for verification to discover the flow attributes but without the necessity for pre-negotiation such as signalling. It has, therefore, an equivalent complexity in implementation at the nodes but does not require the signalling overlay.

The administrative overlay required for policies on bandwidth allocation to the various classes, and reservation of bandwidth for prebooked video sessions, would be no different in complexity to a signalling based system.

Co-existence With RSVP and Administered Connections

Although the dynamic classification can run without the need for signalling, it is also possible to force the classification of the flow as a result of higher level processes. A flow that has been given a reserved path and treatment through the network by signalling or by administration can be marked as such. The automatic classification can be disabled or used to verify the characteristics of the marked flow.

According to the present invention, packet traffic flows are classified in order to group them for differing treatments. This allows quality of service distinctions to be supported even when application signalling support is not available. The implementation is no more complex than that required for policing when signalling is used and may be just as effective in improving perceived network performance and enabling new services such as video.

What is claimed is:

1. In a packet data network for multimedia traffic having one or more nodes, a method of dynamically conditioning traffic comprising steps of:

continuously monitoring the traffic at a node as to its traffic characteristics;

classifying the traffic into one of a plurality of classes which includes two default classes, TCP interactive and UDP low latency, according to preset criteria of traffic characteristics which includes TCP protocol type, UDP protocol type, the length of packets in the traffic and the number of consecutive packets in the traffic, said plurality of classes specifying respective levels of the quality of service with which to condition the traffic; and changing the TCP interactive class to one or the other of TCP bulk guaranteed and TCP bulk best effort, if the traffic contains a series of long packets without an intervening series of two or more short packets.

2. The method according to claim 1 comprising a further step of:

changing the UDP low latency class to one or the other of UDP real time and UDP bulk best effort.

3. The method according to claim 2, comprising a further step of:

delivering downstream the traffic according to the quality of service specified by said one of a plurality of classes.

4. The method according to claim 1 comprising a further step of:

determining a port number which the traffic uses, and classifying the traffic into one of a plurality of classes which includes two default classes, TCP interactive and UDP low latency, according to the port number and preset criteria of traffic characteristics which includes TCP protocol type, UDP protocol type, the length of packets in the traffic and the number of consecutive packets in the traffic, said plurality of classes specifying respective levels of the quality of service with which to condition the traffic.

5. The method according to claim 1 wherein the quality of service is expressed by a plurality of parameters which include a priority level of delivery downstream of the traffic and a bandwidth assigned to the traffic.

6. The method according to claim 1 comprising a further step of:

informing one or more downstream nodes the results of monitoring and classifying.

7. The method according to claim 6 wherein the step of informing comprises a step of:

propagating information relevant to the results in a packet which is inserted into the traffic.

8. In a packet data network for multimedia traffic having one or more nodes, a method of dynamically conditioning traffic comprising steps of:

continuously monitoring the traffic as to its traffic characteristics at a source host from which the traffic is generated;

classifying, at the source host, the traffic into one of a plurality of classes which includes two default classes, TCP interactive and UDP low latency, according to preset criteria of traffic characteristics which includes TCP protocol type, UDP protocol type, the length of packets in the traffic and the number of consecutive packets in the traffic, said plurality of classes specifying respective levels of the quality of service with which to condition the traffic; and changing the TCP interactive class to one or the other of TCP bulk guaranteed and TCP bulk best effort, if the traffic contains a series of long packets without an intervening series of two or more short packets.

9. The method according to claim 8 comprising a further step of:

changing the UDP low latency class to one or the other of UDP real time and UDP bulk best effort.

10. The method according to claim 9 comprising a further step of:

delivering downstream the traffic according to the quality of service specified by said one of a plurality of classes.

11. The method according to claim 8 comprising a further step of:

informing one or more downstream nodes the results of monitoring and classifying.

12. The method according to claim 11 wherein the step of informing comprises a step of:

propagating information relevant to the results in a packet which is inserted into the traffic.

13. The method according to claim 8 comprising a further step of:

determining a port number which the traffic uses, and classifying the traffic into one of a plurality of classes which includes two default classes, TCP interactive and UDP low latency, according to the port number and preset criteria of traffic characteristics which includes TCP protocol type, UDP protocol type, the length of packets in the traffic and the number of consecutive packets in the traffic, said plurality of classes specifying respective levels of the quality of service with which to condition the traffic.

* * * * *